United States Patent [19]

Matassa et al.

[11] Patent Number: 5,614,524

[45] Date of Patent: Mar. 25, 1997

[54] PIPERAZINE DERIVATIVES AS 5-HT$_1$ AGONISTS

[75] Inventors: V. G. Matassa, Rome, Italy; L. J. Street, Harlow; A. J. Reeve, Great Dunmow, both of England

[73] Assignee: Merck Sharp & Dohme Ltd., Hoddesdon, England

[21] Appl. No.: 444,507

[22] Filed: May 19, 1995

[30] Foreign Application Priority Data

May 19, 1994 [GB] United Kingdom ............... 9410031

[51] Int. Cl.$^6$ ............... A61K 31/495; C07D 403/14; C07D 403/04; C07D 403/06

[52] U.S. Cl. ............... 514/253; 544/295; 544/367; 544/369; 544/370; 544/371; 544/372; 544/373; 544/366; 544/374; 544/376

[58] Field of Search ............... 544/295, 367, 544/369, 370, 371, 372, 373, 366, 374, 376; 514/253

[56] References Cited

U.S. PATENT DOCUMENTS

| | | | |
|---|---|---|---|
| 5,364,866 | 11/1994 | Strupczewski et al. | 514/321 |
| 5,418,237 | 5/1995 | Böttcher et al. | 514/253 |
| 5,434,154 | 7/1995 | Smith et al. | 514/249 |
| 5,451,588 | 9/1995 | Baker et al. | 514/321 |

FOREIGN PATENT DOCUMENTS

| | | |
|---|---|---|
| 0438230A2 | 7/1991 | European Pat. Off. . |
| 0494774A1 | 7/1992 | European Pat. Off. . |
| 0497512A2 | 8/1992 | European Pat. Off. . |
| 0548813A1 | 6/1993 | European Pat. Off. . |
| WO/93/18029 | 9/1993 | WIPO . |
| WO/94/03446 | 2/1994 | WIPO . |
| WO/94/02477 | 3/1994 | WIPO . |

*Primary Examiner*—Matthew V. Grumbling
*Attorney, Agent, or Firm*—Robert J. North; Melvin Winokur

[57] ABSTRACT

A class of substituted piperazine derivatives of formula I

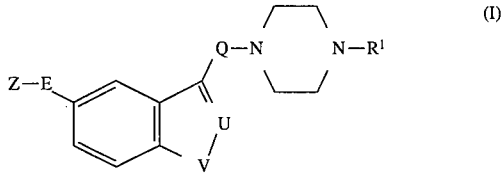

are selective agonists of 5-HT$_1$-like receptors and are therefore useful in the treatment of clinical conditions, in particular migraine and associated conditions, for which a selective agonist of these receptors is indicated.

5 Claims, No Drawings

PIPERAZINE DERIVATIVES AS 5-HT₁ AGONISTS

The present invention relates to a class of substituted piperazine derivatives which act on 5-hydroxytryptamine (5-HT) receptors, being potent and selective agonists of so-called "5-HT₁-like" receptors. They are therefore useful in the treatment of clinical conditions for which a selective agonist of these receptors is indicated.

It has been known for some time that 5-HT₁-like receptor agonists which exhibit selective vasoconstrictor activity are of use in the treatment of migraine (see, for example, A. Doenicke et al., The Lancet, 1988, Vol. 1, 1309–11).

The compounds of the present invention, being potent and selective 5-HT₁-like receptor agonists, are accordingly of particular use in the treatment of migraine and associated conditions, e.g. cluster headache, chronic paroxysmal hemicrania, headache associated with vascular disorders, tension headache and paediatric migraine.

Several distinct classes of substituted five-membered heteroaromatic compounds are described in published European patent applications 0438230, 0497512 and 0494774, and published International patent applications 93/18029, 94/02477 and 94/03446. The compounds described therein are stated to be agonists of 5-HT₁-like receptors, and accordingly to be of particular use in the treatment of migraine and associated conditions. None of these publications, however, discloses nor even suggests the piperazine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with any other substituent; nor is there any suggestion therein that the range of substituents specified at the 5-position of the indole moiety might be successfully replaced by an optionally substituted five-membered heteroaromatic ring.

The present invention provides a compound of formula I, or a salt or prodrug thereof:

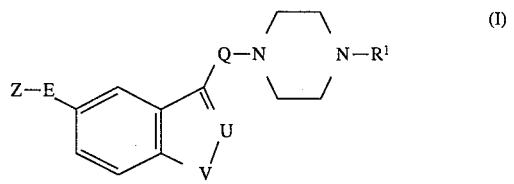

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 6 carbon atoms;

U represents nitrogen or C—R²;

V represents oxygen, sulphur or N—R³;

R¹ represents cyano($C_{1-6}$)alkyl, amino($C_{1-6}$)alkyl, $C_{2-6}$ alkylcarbonylamino($C_{1-6}$)alkyl or $C_{2-6}$ alkoxycarbonylamino($C_{1-6}$)alkyl, or an optionally substituted pyrimidinyl moiety; and R² and R³ independently represent hydrogen or $C_{1-6}$ alkyl.

The five-membered heteroaromatic ring Z in the compounds of formula I above may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl.

When R¹ represents an optionally substituted pyrimidinyl moiety, this is suitably an optionally substituted pyrimidin-2-yl, pyrimidin-4-yl or pyrimidin-5-yl moiety, preferably pyrimidin-2-yl. The pyrimidinyl moiety R¹ may be optionally substituted by one or more substituents. Examples of optional substituents on the pyrimidinyl moiety R¹ include halogen, cyano, trifluoromethyl, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$)alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$)alkylaminosulphonyl, aminosulphonylmethyl, $C_{1-6}$ alkylaminosulphonylmethyl and di($C_{1-6}$)alkylaminosulphonylmethyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl and allyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenethyl, phenylpropyl and naphthylmethyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The optionally substituted five-membered heteroaromatic ring Z in formula I is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

Where E and Q, which may be the same or different, represent straight or branched alkylene chains, these may be, for example, methylene, ethylene, 1-methylethylene, propylene, 2-methylpropylene or butylene. In addition, E may represent a chemical bond such that the moiety Z is attached directly to the benzo moiety of the central fused bicyclic heteroaromatic ring system.

The compound of formula I in accordance with the present invention is suitably an indole, benzofuran or benzthiophene derivative of formula IA, or an indazole derivative of formula IB:

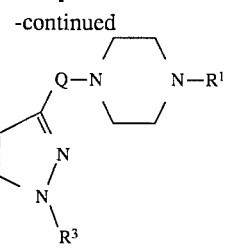

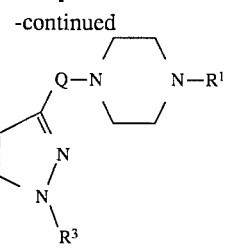

wherein Z, E, Q, V, $R^1$, $R^2$ and $R^3$ are as defined above.

Preferably, the compounds according to the invention are indole derivatives of formula IC:

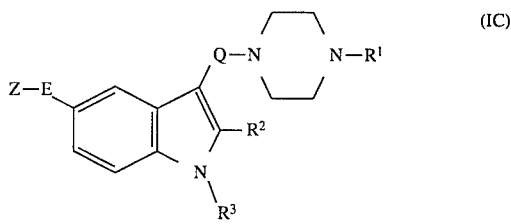

wherein Z, E, Q, $R^1$, $R^2$ and $R^3$ are as defined above, in particular wherein $R^2$ and $R^3$ are both hydrogen.

When $R^1$ represents an optionally substituted pyrimidinyl moiety, the pyrimidine ring is suitably unsubstituted.

Particular values for the substituent $R^1$ include cyanomethyl, aminoethyl, acetylamino-ethyl, t-butoxycarbonylamino-ethyl and pyrimidin-2-yl.

Suitably, $R^2$ and $R^3$ independently represent hydrogen or methyl, especially hydrogen.

A particular sub-class of compounds according to the invention is represented by the compounds of formula IIA, and salts and prodrugs thereof:

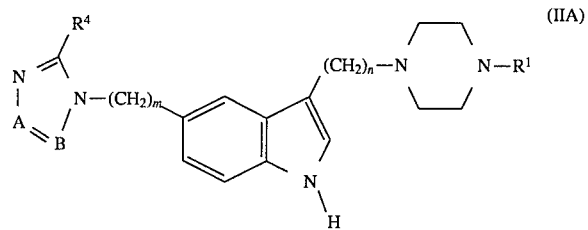

wherein
$R^1$ is as defined with reference to formula I above;
m is zero, 1, 2 or 3;
n is 2, 3, 4 or 5;
A represents nitrogen or CH;
B represents nitrogen or C—$R^5$; and
$R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl.

Particular values of $R^4$ and $R^5$ include hydrogen, methyl, ethyl, benzyl and amino, especially hydrogen.

Specific compounds within the scope of the present invention include:

1-[3-(5-(1,2,4-triazol-4-yl)-1H-indol-3-yl)propyl]-4-(pyrimidin-2-yl)piperazine;

1-[3-(5-(1,2,4- triazol-4-yl)-1H-indol-3-yl)propyl]-4-[2-(N-tert-butoxycarbonylamino)ethyl]piperazine;

1-[3-(5-(1,2,4-triazol-4-yl)-1H-indol-3-yl)propyl]-4-(2-aminoethyl)piperazine;

1-[3-(5-(1,2,4-triazol-4-yl)-1H-indol-3-yl)propyl]-4-[2-(acetylamino)ethyl]piperazine;

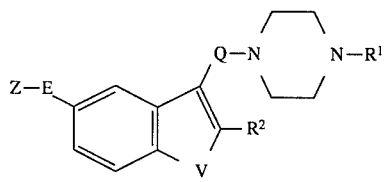

1-[3-(5-(1,2,4-triazol-4-yl)-1H-indol-3-yl)propyl]-4-cyanomethylpiperazine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises attachment of the $R^1$ moiety by conventional means to a compound of formula III:

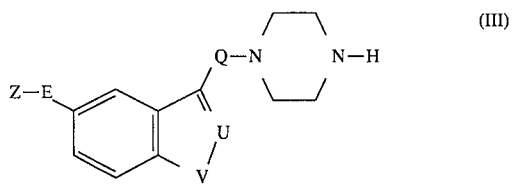

wherein Z, E, Q, U and V are as defined above.

Attachment of the $R^1$ moiety to the compounds of formula III may conveniently be effected by standard alkylation techniques, for example by treatment with an appropriate alkyl halide such as bromoacetonitrile, typically under basic conditions, e.g. sodium hydride in N,N-dimethylformamide, or triethylamine in acetonitrile. Alternatively, the $R^1$ moiety may conveniently be attached by a reductive alkylation procedure, which comprises treating the required compound of formula III as defined above with the appropriate aldehyde in the presence of a reducing agent such as sodium cyanoborohydride. Where $R^1$ represents an optionally substituted pyrimidin-2-yl moiety, attachment thereof may suitably be effected by reacting compound III with the appropriate 2-halopyrimidine, for example 2-chloropyrimidine, typically in the presence of a base such as sodium carbonate.

The compounds of formula III above wherein U represents C—$R^2$ and V represents N—$R^3$, corresponding to the indole derivatives of formula IC as defined above wherein $R^1$ is hydrogen, may be prepared by a process which comprises reacting a compound of formula IV:

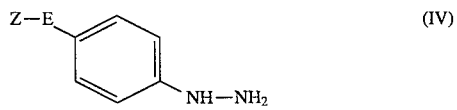

wherein Z and E are as defined above; with a compound of formula V, or a carbonyl-protected form thereof:

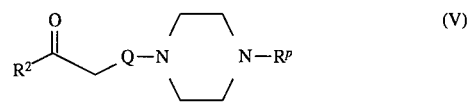

wherein $R^2$ and Q are as defined above, and $R^p$ represents an amino-protecting group; followed, where required, by N-alkylation by standard methods to introduce the moiety $R^3$; with subsequent removal of the amino-protecting group $R^p$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group $R^p$ in the compounds of formula V is suitably a carbamoyl moiety such as t-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

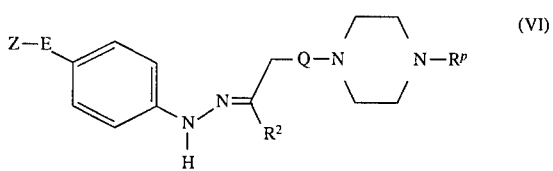

(VI)

wherein Z, E, Q, R² and Rᵖ are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

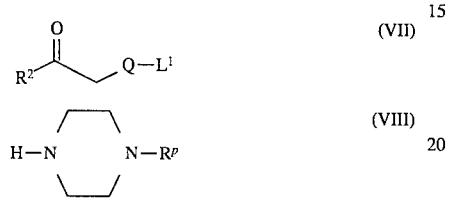

(VII)

(VIII)

wherein Q, R² and Rᵖ are as defined above, and L¹ represents a suitable leaving group.

The leaving group L¹ is suitably a halogen atom, e.g. chlorine or bromine.

Where L¹ represents a halogen atom, the reaction between compounds VII and VIII is conveniently effected by stirring the reactants under basic conditions in a suitable solvent, for example potassium carbonate in N,N-dimethylformamide, or triethylamine in tetrahydrofuran or acetonitrile.

The compounds according to the invention wherein U represents C—R² and V represents N—R³—i.e. the indole derivatives of formula IC as defined above—may alternatively be prepared by a process which comprises reacting a compound of formula IV as defined above with a compound of formula IX, or a carbonyl-protected form thereof:

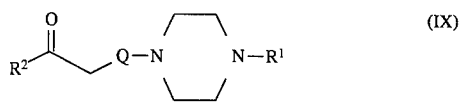

(IX)

wherein Q, R¹ and R² are as defined above; under conditions analogous to those described above for the reaction between compounds IV and V; followed, where required, by N-alkylation by standard methods to introduce the moiety R³.

As for the compounds of formula V, suitable carbonyl-protected forms of the compounds of formula IX include the dimethyl acetal or ketal derivatives.

As with that between compounds IV and V, the Fischer reaction between compounds IV and IX may be carried out in a single step, or may proceed via an initial non-cyclising step at a lower temperature to give an intermediate of formula X:

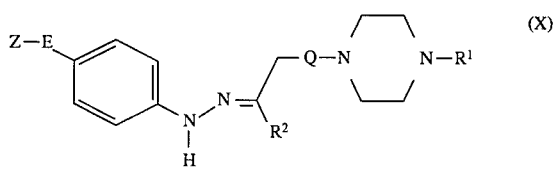

(X)

wherein Z, E, Q, R¹ and R² are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

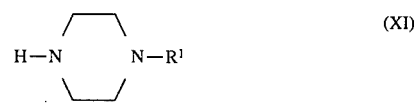

(XI)

wherein R¹ is as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

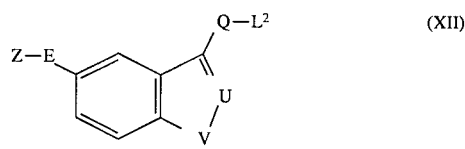

(XII)

wherein Z, E, Q, U and V are as defined above, and L² represents a suitable leaving group; followed by removal of the amino-protecting group Rᵖ.

Similarly, the compounds of formula I as defined above may be prepared by a process which comprises reacting a compound of formula XI as defined above with a compound of formula XII as defined above.

The leaving group L² is suitably an alkylsulphonyloxy or arylsulphonyloxy group, e.g. methanesulphonyloxy (mesyloxy) or p-toluenesulphonyloxy (tosyloxy).

Where L² represents an alkylsulphonyloxy or arylsulphonyloxy group, the reaction between compound XII and compound VIII or XI is conveniently carried out in a suitable solvent such as 1,2-dimethoxyethane, typically in the presence of a base such as sodium carbonate.

In a representative embodiment, the compounds of formula XII wherein U represents CH, V represents NH, Q represents a propylene chain and L² represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating an acid addition salt of the hydrazine derivative IV, typically the hydrochloride salt, in an inert solvent such as dioxan, at the reflux temperature of the solvent.

In a further procedure, the compounds of formula III above wherein U represents nitrogen and V represents N—R³, corresponding to the indazole derivatives of formula IB as defined above wherein R¹ is hydrogen, may be prepared by a process which comprises cyclising a compound of formula XIII:

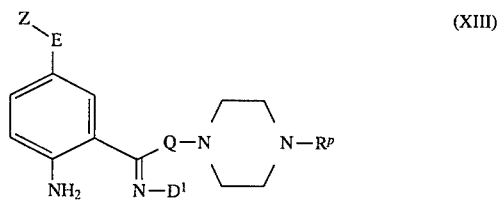

(XIII)

wherein Z, E, Q and $R^p$ are as defined above, and $D^1$ represents a readily displaceable group; followed, where required, by N-alkylation by standard methods to introduce the moiety $R^3$; with subsequent removal of the amino-protecting group $R^p$.

Similarly, the compounds of formula I wherein U represents nitrogen and V represents N—$R^3$—i.e. the indazole derivatives of formula IB as defined above—may be prepared by a process which comprises cyclising a compound of formula XIV:

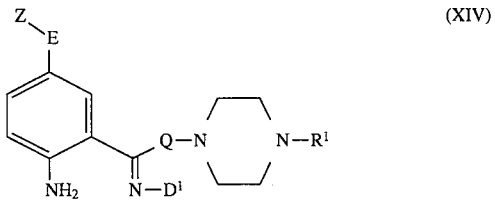

in which Z, E, Q, $R^1$ and $D^1$ are as defined above.

The cyclisation of compounds XIII and XIV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIII and XIV suitably represents a $C_{1-4}$ alkanoyloxy group, preferably acetoxy. Where $D^1$ represents acetoxy, the desired compound of formula XIII or XIV may be conveniently prepared by treating a carbonyl compound of formula XV:

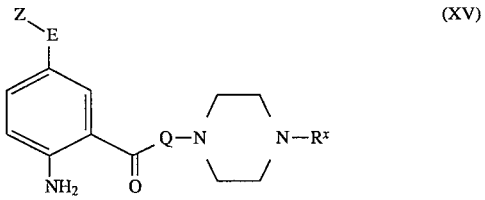

wherein Z, E and Q are as defined above, and $R^x$ corresponds to the group $R^1$ as defined above or represents an amino-protecting group as defined for $R^p$; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XV may conveniently be prepared by ozonolysis of the corresponding indole derivative of formula XVI:

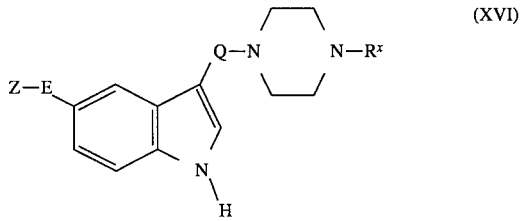

wherein Z, E, Q and $R^x$ are as defined above; followed by a reductive work-up, advantageously using dimethylsulphide.

The indole derivatives of formula XVI may be prepared by methods analogous to those described in the accompanying Examples, or by procedures well known from the art.

In a still further procedure, the compounds of formula III above wherein U represents C—$R^2$ and V represents oxygen or sulphur, corresponding to the benzofuran or benzthiophene derivatives of formula IA wherein V is oxygen or sulphur respectively and $R^1$ is hydrogen, may be prepared by a process which comprises cyclising a compound of formula XVII:

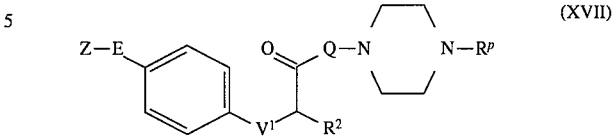

wherein Z, E, Q, $R^2$ and $R^p$ are as defined above, and $V^1$ represents oxygen or sulphur; followed by removal of the amino-protecting group $R^p$.

Similarly, the compounds of formula I wherein U represents C—$R^2$ and V represents oxygen or sulphur—i.e. the benzofuran or benzthiophene derivatives of formula IA above—may be prepared by a process which comprises cyclising a compound of formula XVIII:

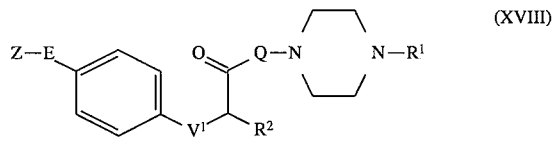

wherein Z, E, Q, $R^1$, $R^2$ and $V^1$ are as defined above.

The cyclisation of compounds XVII and XVIII is conveniently effected by using polyphosphoric acid or a polyphosphate ester, advantageously at an elevated temperature.

The compounds of formula XVII and XVIII may be prepared by reacting a compound of formula XIX with a compound of formula XX:

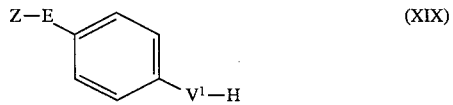

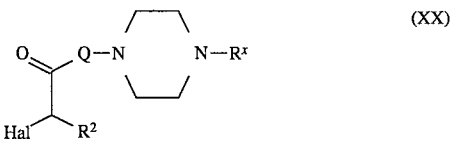

wherein Z, E, Q, $R^2$, $V^1$ and $R^x$ are as defined above, and Hal represents a halogen atom.

The reaction is conveniently effected in the presence of a base such as sodium hydroxide.

The hydroxy and mercapto derivatives of formula XIX may be prepared by a variety of methods which will be readily apparent to those skilled in the art. One such method is described in EP-A-0497512.

The hydrazine derivatives of formula IV above may be prepared by methods analogous to those described in EP-A-0438230 and EP-A-0497512.

Where they are not commercially available, the starting materials of formula VII, VIII, XI and XX may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein $R^1$ is t-butoxycarbonylamino($C_{1-6}$)alkyl originally obtained may be converted into the corresponding compound wherein $R^1$ represents amino($C_{1-6}$)alkyl, suitably by acidic hydrolysis; and this compound may in turn be converted into the corresponding acetylamino($C_{1-6}$)alkyl derivative by means of standard acetylation procedures. Furthermore, a compound of formula I initially obtained wherein $R^1$ represents, for example, cyanomethyl may be converted into the corresponding compound wherein $R^1$ represents aminoethyl by reduction, typically using lithium aluminium hydride. In addition, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Orgasmic Synthesis*, John Wiley & Sons, 1991. The protecting groups may be removed at a convenient subsequent stage using methods known from the art.

The following Examples illustrate the preparation of compounds according to the invention.

EXAMPLE 1

1-(3-[5-(1,2,4-Triazol-4-yl)-1H-indol-3-yl]propyl)-4-(pyrimidin-2-yl)piperazine, 2.2 Hydrogen Oxalate, 0.25 Hydrate 1. Intermediate 1: 4'-(1,2,4-Triazol-4-yl)phenylhydrazine a) 4'-Aminoacetanilide A solution of 4-nitroacetanilide (5.0 g, 27.8 mmol) in EtOH/EtOAc (160 ml, 1:1), $H_2O$ (15 ml) and 5N HCl (5.6 ml, 28.0 mmol) was hydrogenated over 10% Pd-C (0.50 g) at 50 psi for 0.25 h. The catalyst was removed by filtration through celite and the solvents removed under vacuum. The free base was generated by dissolving the product in $H_2O$, basifying with 2N NaOH and extracting into EtOAc. The combined extracts were dried ($MgSO_4$) and evaporated to give the title-aniline (3.75 g, 90%). δ (250 MHz, $CDCl_3/d_4$-MeOH) 2.10 (3H, s, Me); 6.68 (2H, d, J=8.8 Hz, Ar-H); 7.27 (2H, d, J=8.8 Hz, Ar-H).

b) 4'-(1,2,4-Triazol-4-yl)acetanilide

A mixture of the preceding aniline (3.52 g, 23.4 mmol), N,N-dimethylformamide azine (3.33 g, 23.4 mmol; *J. Chem. Soc. (C)*, 1967, 1664) and p-toluenesulphonic acid monohydrate (0.223 g, 1.17 mmol), in anhydrous toluene (100 ml) was heated at reflux for 17 h. The beige coloured precipitate was filtered off and washed with toluene and $CH_2Cl_2$ and dried under vacuum to give the desired triazole (4.29 g, 91%); δ (250 MHz, $d_4$-MeOH/$d_6$-DMSO) 2.14 (3H, s, $CH_3$); 7.60 (2H, d, J=8.8 Hz, Ar-H); 7.78 (2H, d, J=8.8 Hz, Ar-H); 8.96 (2H, s, Ar-H).

c) 4'-(1,2,4-Triazol-4-yl)phenylaniline

A solution of the preceding acetanilide (4.91 g, 24.3 mmol) in 5N HCl (100 ml) was heated at 125° C. for 1.5 h. The mixture was cooled to 0° C., basified with concentrated aqueous NaOH solution and extracted with $CH_2Cl_2$ (x 5). The combined extracts were dried ($MgSO_4$) and evaporated and the residue chromatographed on silica gel, eluting with $CH_2Cl_2$/MeOH/$NH_3$ (80:8:1), to give the title-aniline (2.94 g, 76%); δ (250 MHz, $CDCl_3$) 3.80 (2H, s, $NH_2$); 6.71 (2H, d, J=8.8 Hz, Ar-H); 7.08 (2H, d, J=8.8 Hz, Ar-H); 8.36 (2H, s, Ar-H).

d) 4'-(1,2,4-Triazol-4-yl)phenylhydrazine

To a solution of the preceding aniline (1.60 g, 9.99 mmol) in concentrated HCl/$H_2O$ (23 ml and 3 ml respectively) was added, at −21° C., a solution of $NaNO_2$ (0.69 g, 9.99 mmol) in $H_2O$ (8 ml), at such a rate as to maintain the temperature below −10° C. The mixture was stirred for 0.3 h and then filtered rapidly through a sinter, under vacuum. The filtrate was added to a cooled (−20° C.) solution of $SnCl_2.2H_2O$ (9.02 g, 40.0 mmol) in concentrated HCl (17 ml). The mixture was stirred at −20° C. for 0.25 h and then at room temperature for 1.25 h. The resulting solid was filtered off, washed with $Et_2O$ and dried under vacuum. The crude product was dissolved in $H_2O$, basified with concentrated aqueous NaOH and extracted with EtOAc (x 5). The combined extracts were dried ($MgSO_4$) and evaporated to afford the title-product (0.95 g, 54%); δ (250 MHz, $CDCl_3/d_4$-MeOH) 3.98 (3H, br s, NH and $NH_2$); 6.97 (2H, d, J=12.0 Hz, Ar-H); 7.25 (2H, d, J=12.0 Hz, Ar-H); 8.48 (2H, s, Ar-H).

2. Intermediate 2: 1-(3-[5-(1,2,4-Triazol-4-yl)-1H-indol-3-yl]propyl)-4-(H)-piperazine. 3.5 Hydrogen Oxalate 1. 5-(4-tert-Butyloxycarbonyl)piperazin-1-yl pentanal dimethyl acetal a) 5-Bromopentanal dimethyl acetal To a solution of 5-bromovaleryl chloride (50 g, 0.251 mol) in anhydrous THF (500 ml), at −78° C., was added lithium tri-tert-butoxyaluminohydride (1.0M solution in tetrahydrofuran, 300 ml; 0.30 mol), keeping the temperature below −70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (x 2). The combined extracts were washed with saturated $Na_2CO_3$ solution (x 1), water (x 1) and brine (x 2), dried ($Na_2SO_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added $K_2CO_3$ solution (50 ml) and diethyl ether (500 ml). The aqueous layer was separated and re-extracted with ether (x 2). The combined extracts were washed with water and brine, dried ($Na_2SO_4$) and evaporated. The crude product was chromatographed on silica gel eluting with diethyl ether/hexane (1:9) to give the title-acetal (27.5 g, 57%). δ (250 MHz, $CDCl_3$) 1.43–1.67 (4H, m, 2 of $CH_2$); 1.83–1.94 (2H, m, $CH_2$); 3.38 (6H, s, $CH(OMe)_2$); 3.42 (2H, t, J=7 Hz, $CH_2Br$), 4.37 (1H, t, J=7 Hz, $CH(OMe)_2$).

b) 5-(4-tert-Butyloxycarbonyl)piperazin-1-yl pentanal dimethyl acetal

A mixture of 5-bromovaleraldehyde dimethyl acetal (27.5 g, 0.13 mol), $Na_2CO_3$ (20.7 g, 0.195 mol), sodium iodide (19.5 g, 0.13 mol) and tert-butyl-1-piperazinecarboxylate (25.5 g, 0.137 mol), in dimethoxyethane (250 ml), was heated at 100° C. for 3 h. Aluminium foil was wrapped around the vessel to exclude light. The mixture was cooled to room temperature and filtered. The filtrate was evaporated under reduced pressure and then EtOAc (50 ml) added and the mixture filtered again to remove inorganic salts. The solvent was removed under vacuum and the residue chromatographed on silica gel eluting with EtOAc to give the title-product (25.7 g, 63%). δ (250 MHz, $CDCl_3$) 1.29–1.71 (6H, m, 3 of $CH_2$); 1.46 (9H, s, $OC(Me)_3$); 2.31–2.39 (6H, m, 3 of $CH_2$); 3.32 (6H, s, $CH(OMe)_2$); 3.41–3.45 (4H, m, 2 of $CH_2$); 4.36 (1H, t, J=6 Hz, $CH(OMe)_2$).

2. 1-(3-[5-(1,2,4-Triazol-4-yl)-1H-indol-3-yl]propyl)-4-(H)-piperazine. 3.5 Hydrogen Oxalate A mixture of intermediate 1 (5.0 g, 28.6 mmol) and 5-(4-tert-butyloxycarbonyl)piperazin-1-yl pentanal dimethyl acetal (9.03 g, 28.6 mmol) in 4% sulphuric acid (150 ml) was heated at reflux for 48 h. The solution was cooled in an ice-bath, basified with solid $K_2CO_3$ and extracted with butan-1-ol (x 3). The solvent was removed under vacuum and azeotroped with hexane (x 2). The crude product was purified by chromatography on silica gel eluting with $CH_2Cl_2$/MeOH/$NH_3$ (30:8:1) to give the title-indole (3.9 g, 44%). The 3.5 hydrogen oxalate salt was prepared using 200 mg of free base: mp 90°–92° C. (Found: C, 45.97; H, 4.76; N, 13.77. $C_{17}H_{22}N_6.3.5(C_2H_2O_4)$ requires C, 46.08; H, 4.76; N, 13.43%); δ (360 MHz, $D_2O$) 2.12–2.24 (2H, m, $CH_2$); 2.93 (2H, t, J=7 Hz, $CH_2$); 3.46–3.76 (8H, m, 4 of $CH_2$); 7.37 (1H, dd, J=1.9 and 8.7 Hz, Ar-H); 7.39 (1H, s, Ar-H); 7.66 (1H, d, J=8.7, Ar-H); 7.82 (1H, d, J=1.9 Hz, Ar-H); 9.13 (2H, s, Triazole-H).

3. 1-(3-[5-(1,2,4-Triazol-4-yl)-1H-indol-3-yl]propyl)-4-(pyrimidin-2-yl)piperazine. 2.2 Hydrogen Oxalate 0.25 Hydrate A mixture of Intermediate 2 (0.15 g, 0.48 mmol), 2-chloropyrimidine (0.066 g, 0.58 mmol) and $Na_2CO_3$ (0.072 g, 0.68 mmol), in methanol was heated at reflux for 16 h. The solvent was removed under vacuum and the residue partitioned between ethyl acetate and water. The organic layer was separated and washed with water (x 1) and brine (x 1), dried ($Na_2SO_4$) and evaporated. Chromatography of the crude product on silica gel eluting with $CH_2Cl_2$/MeOH/$NH_3$ (60:8:1) gave the title-piperazine (0.025 g, 13%). The 2.2 hydrogen oxalate 0.25 hydrate salt was prepared: mp 79°–81° C. (Found: C, 51.99; H, 5.39; N, 18.78. $C_{21}H_{24}N_8.2.2(C_2H_2O_4).0.25 H_2O$ requires C, 51.61; H, 4.99; N, 18.95%); m/e 389 (M+1)$^+$; δ (360 MHz, $D_2O$) 2.12–2.26 (2H, m, $CH_2$); 2.86–2.98 (2H, m, $CH_2$); 3.08–3.80 (8H, m, 4 of $CH_2$); 4.58–4.70 (2H, m, $CH_2$); 7.01 (1H, t, J=5.0 Hz, Pyrimidine-H); 7.38 (1H, d, J=8.6 Hz, Ar-H); 7.41 (1H, s, Ar-H); 7.67 (1H, d, J=8.6 Hz, Ar-H); 7.87 (1H, s, Ar-H); 8.52 (2H, d, J=5.0 Hz, Pyrimidine-H); 9.47 (2H, s, Triazole-H).

EXAMPLE 2

1-(3-[5-(1,2,4-Triazol-4-yl)-1H-indol-3-yl]propyl)-4-(2-(N-tert-butyloxycarbonylamino)ethyl)piperazine 3.1 Hydrogen Oxalate. Hemihydrate A mixture of Intermediate 2 (0.3 g, 0.97 mmol), $K_2CO_3$ (0.268 g, 1.94 mmol), and N-tert-butyloxycarbonylamino-2-bromoethane (0.26 g, 1.16 mmol), in DMF (10 ml) was heated at 80° C. for 2 h. The mixture was cooled to room temperature and water (50 ml) and EtOAc (50 ml) were added. The aqueous was separated and extracted further with EtOAc (x 3). The combined extracts were dried ($Na_2SO_4$) and evaporated and the residue chromatographed on silica gel eluting with $CH_2Cl_2$/MeOH/$NH_3$ (60:8:1) to give the title-product (0.189 g, 43%). The 3.1 hydrogen oxalate hemihydrate salt was prepared: mp 155°–158° C. (Found: C, 49.02; H, 5.82; N, 12.96. $C_{24}H_{35}N_7O_2.3.1(C_2H_2O_4).0.5 H_2O$ requires C, 48.91; H, 5.74; N, 13.22%); m/e 454 (M+1)$^+$; δ (360 MHz, $d_6$-DMSO) 1.37 (9H, s, $OC(Me)_3$); 1.94–2.06 (2H, m, $CH_2$); 2.50–3.20 (16H, m, 8 of $CH_2$); 6.70–6.76 (1H, m, NHBOC); 7.32 (1H, dd, J=2.1 and 8.7 Hz, Ar-H); 7.33 (1H, s, Ar-H); 7.50 (1H, d, J=8.7 Hz, Ar-H); 7.79 (1H, d, J=2.1 Hz, Ar-H); 9.01 (2H, s, Triazole-H); 11.17 (1H, s, NH).

EXAMPLE 3

1-(3-[5-(1,2,4-Triazol-4-yl)-1H-indol-3-yl]propyl)-4-(2-(amino)ethyl)piperazine, 2.5 Hydrogen Oxalate. 0.75 Hydrate A solution of Example 2 (0.36 g, 0.8 mmol) in 99% formic acid (10 ml) was stirred at room temperature for 16 h. The formic acid was removed under vacuum, saturated $K_2CO_3$ solution (20 ml) added to the residue and extracted with n-butanol (x 3). The solvent was evaporated under reduced pressure and azeotroped with hexane (x 1) and ethanol (x 1). The crude product was chromatographed on silica gel eluting with $CH_2Cl_2$/MeOH/$NH_3$ (30:8:1) to give the title-piperazine (0.246 g, 88%). The 2.5 hydrogen oxalate 0.75 hydrate salt was prepared: mp 120°–125° C. (hygroscopic). (Found: C, 48.60; H, 5.98; N, 16.76. $C_{19}H_{27}N_7.2.5(C_2H_2O_4).0.75 H_2O$ requires C, 48.69; H, 5.70; N, 16.56%); δ (360 MHz, $d_6$-DMSO) 1.96–2.08 (2H, m, $CH_2$); 2.46–3.18 (16H, m, 8 of $CH_2$); 7.32(1H, dd, J=2.1 and 8.8 Hz, Ar-H); 7.33 (1H, s, Ar-H); 7.50 (1H, d, J=8.8 Hz, Ar-H); 7.81 (1H, d, J=2.1 Hz, Ar-H); 9.02 (2H, s, Triazole-H); 11.18 (1H, s, NH).

EXAMPLE 4

1-(3-[5-(1,2,4-Triazol-4-yl)-1H-indol-3-yl]propyl)-4-(2-acetamido)ethyl)piperazine. Bishydrogen Oxalate. 0.75 Hydrate Acetyl chloride (0.028 g, 0.36 mmol) was added to a solution of Example 3 (0.12 g, 0.34 mmol) and pyridine (0.028 g, 0.35 mmol), in $CH_2Cl_2$ (15 ml), at +5° C. The mixture was warmed to room temperature and stirred for 1 h before adding saturated $K_2CO_3$ solution (5 ml) and extracting with $CH_2Cl_2$ (x 3). The combined extracts were dried ($Na_2SO_4$) and evaporated and the residue chromatographed on silica gel eluting with $CH_2Cl_2$/MeOH/$NH_3$ (50:8:1) to give the title-acetamide (0.045 g, 34%). The bis hydrogen oxalate 0.75 hydrate salt was prepared: mp 199°–202° C. (Found: C, 51.15; H, 6.08; N, 16.87. $C_{21}H_{29}N_7O.2(C_2H_2O_4).0.75 H_2O$ requires C, 50.97; H, 5.90; N, 16.64%); m/e 396 (M+1)$^+$; δ (360 MHz, $d_6$-DMSO) 1.79 (3H, s, NHCOMe), 1.88–2.04 (2H, m, $CH_2$); 2.42–3.28 (16H, m, 8 of $CH_2$); 7.32 (1H, dd, J=2.1 and 8.6 Hz, Ar-H); 7.33 (1H, s, Ar-H); 7.50 (1H, d, J=8.6 Hz, Ar-H); 7.80 (1H, d, J=2.1 Hz, Ar-H); 7.85 (1H, br s, NHCOMe); 9.02 (2H, s, Triazole-H); 11.18 (1H, s, NH).

EXAMPLE 5

1-(3-[5-(1,2,4-Triazol-4-yl)-1H-indol-3-yl]propyl)-4-(cyanomethyl)piperazine. Sesquioxalate. 0.55 Hydrate The title-compound was prepared from Intermediate 2 and bromoacetonitrile using the procedure described for Example 2. The product was obtained in 71% yield and the sesquioxalate 0.55 hydrate salt prepared: mp 89°–91° C. (Found: C, 53.24; H, 5.37; N, 19.84. $C_{19}H_{23}N_7.1.5(C_2H_2O_4).0.55\ H_2O$ requires C, 53.45; H, 5.53; N, 19.83%); m/e 350 (M+1)$^+$; δ (360 MHz, D$_2$O) 2.06–2.18 (2H, m, CH$_2$); 2.60–2.74 (2H, m, CH$_2$); 2.86 (2H, t, J=7.1 Hz, CH$_2$); 2.98–3.24 (6H, m, 3 of CH$_2$); 3.50–3.64 (2H, m, CH$_2$); 3.77 (2H, s, CH$_2$CN); 7.29 (1H, dd, J=2.0 and 8.6 Hz, Ar-H); 7.34 (1H, s, Ar-H); 7.59 (1H, d, J=8.6 Hz, Ar-H); 7.74 (1H, d, J=2.0 Hz, Ar-H); 9.01 (2H, s, Triazole-H).

What is claimed is:

1. A compound of formula I, or a pharmaceutically-acceptable salt or prodrug thereof:

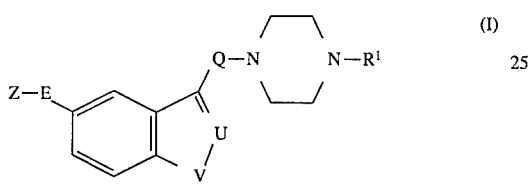

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 6 carbon atoms;

U represents C—R$^2$;

V represents N—R$^3$;

R$^1$ represents cyano(C$_{1-6}$)alkyl, amino(C$_{1-6}$)alkyl, C$_{2-6}$ alkylcarbonylamino(C$_{1-6}$)alkyl or C$_{2-6}$ alkoxycarbonylamino(C$_{1-6}$)alkyl, or an optionally substituted pyrimidinyl moiety; and R$^2$ and R$^3$ independently represent hydrogen or C$_{1-6}$ alkyl.

2. A compound as claimed in claim 1 represented by formula IIA pharmaceutically-acceptable, and salts and prodrugs thereof:

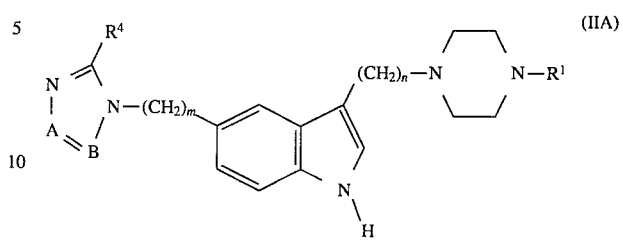

wherein

R$^1$ is as defined in claim 1;

m is zero, 1, 2 or 3;

n is 2, 3, 4 or 5;

A represents nitrogen or CH;

B represents nitrogen or C—R$^5$; and

R$^4$ and R$^5$ independently represent hydrogen, C$_{1-6}$ alkyl, C$_{2-6}$ alkenyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{1-6}$ alkoxy, C$_{1-6}$ alkylthio, amino, C$_{1-6}$ alkylamino, di(C$_{1-6}$)alkylamino, halogen, cyano or trifluoromethyl.

3. A compound as claimed in claim 1 selected from:

1-[3-(5-(1,2,4-triazol-4-yl)-1H-indol-3-yl)propyl]-4-(pyrimidin-2-yl)piperazine;

1-[3-(5-(1,2,4-triazol-4-yl)-1H-indol-3-yl)propyl]-4-[2-(N-tert-butoxycarbonylamino)ethyl]piperazine;

1-[3-(5-(1,2,4-triazol-4-yl)-1H-indol-3-yl)propyl]-4-(2-aminoethyl)piperazine;

1-[3-(5-(1,2,4-triazol-4-yl)-1H-indol-3-yl)propyl]-4-[2-(acetylamino)ethyl]piperazine;

1-[3-(5-(1,2,4-triazol-4-yl)-1H-indol-3-yl)propyl]-4-cyanomethylpiperazine;

and pharmaceutically-acceptable salts and prodrugs thereof.

4. A pharmaceutical composition comprising an effective amount a compound as claimed in claim 1 in association with a pharmaceutically acceptable carrier.

5. A method for the treatment and/or prevention of clinical conditions for which a selective agonist of 5-HT$_1$-like receptors is indicated, which comprises administering to a patient in need of such treatment an effective amount of a compound as claimed in claim 1.

* * * * *